United States Patent
Jiang et al.

(10) Patent No.: US 10,646,449 B2
(45) Date of Patent: May 12, 2020

(54) RICE BRAN STEROL SUGAR-COATED TABLET

(71) Applicant: Hangzhou Yipin Xinwufeng Pharmaceutical Co., Ltd., Zhejiang (CN)

(72) Inventors: Weixing Jiang, Zhejiang (CN); Long Jiang, Zhejiang (CN); Aiqin Shi, Zhejiang (CN); Zhiqiang Mo, Zhejiang (CN)

(73) Assignee: Hangzhou Yipin Xinwufeng Pharmaceutical Co., Ltd., Zhejiang (CN)

( * ) Notice: Subject to any disclaimer, the term of this patent is extended or adjusted under 35 U.S.C. 154(b) by 12 days.

(21) Appl. No.: 15/955,698

(22) Filed: Apr. 18, 2018

(65) Prior Publication Data

US 2018/0235890 A1  Aug. 23, 2018

Related U.S. Application Data

(63) Continuation of application No. PCT/CN2017/083509, filed on May 8, 2017.

(30) Foreign Application Priority Data

Nov. 28, 2016 (CN) .......................... 2016 1 1061181

(51) Int. Cl.
- A61K 9/28 (2006.01)
- A61K 36/899 (2006.01)
- A61P 1/00 (2006.01)
- A61K 31/575 (2006.01)
- A61P 1/02 (2006.01)
- A61K 9/20 (2006.01)

(52) U.S. Cl.
CPC .......... *A61K 9/2826* (2013.01); *A61K 9/2054* (2013.01); *A61K 9/2059* (2013.01); *A61K 9/2893* (2013.01); *A61K 31/575* (2013.01); *A61K 36/899* (2013.01); *A61P 1/00* (2018.01); *A61P 1/02* (2018.01)

(58) Field of Classification Search
CPC combination set(s) only.
See application file for complete search history.

(56) References Cited

FOREIGN PATENT DOCUMENTS

| CN | 1634076 | 7/2005 |
| CN | 1788715 | 6/2006 |
| CN | 105727271 | 7/2016 |
| CN | 106491552 | 3/2017 |

OTHER PUBLICATIONS

Postherpetic Neuralgia article from Merck Manual [online], downloaded on Jul. 15, 2019 from URL <https://www.merckmanuals.com/home/infections/herpesvirus-infections/postherpetic-neuralgia?query=neuralgia>.*
Glassopharyngeal neuralgia article from Merck Manual [online], downloaded on Jul. 15, 2019 from URL <https://www.merckmanuals.com/home/brain,-spinal-cord,-and-nerve-disorders/cranial-nerve-disorders/glossopharyngeal-neuralgia?query=neuralgia>.*
Trigeminal Neuralgia article from Merck Manual [online], downloaded on Jul. 15, 2019 from URL <https://www.merckmanuals.com/home/brain,-spinal-cord,-and-nerve-disorders/cranial-nerve-disorders/trigeminal-neuralgia?query=neuralgia>.*
Neuropathic Pain article from Merck Manual [online], downloaded on Jul. 15, 2019 from URL <https://www.merckmanuals.com/professional/neurologic-disorders/pain/neuropathic-pain>.*
Mononeuropathy article from Merck Manual [online], downloaded on Jul. 15, 2019 from URL <https://www.merckmanuals.com/home/brain,-spinal-cord,-and-nerve-disorders/peripheral-nerve-disorders/mononeuropathy?query=Mononeuropathies>.*
Polyneuropathy article from Merck Manual [online], downloaded on Jul. 15, 2019 from URL <<https://www.merckmanuals.com/home/brain,-spinal-cord,-and-nerve-disorders/peripheral-nerve-disorders/polyneuropathy?query=Polyneuropathy>.*
Multiple Mononeuropathy article from Merck Manual [online], downloaded on Jul. 15, 2019 from URL <https://www.merckmanuals.com/home/brain,-spinal-cord,-and-nerve-disorders/peripheral-nerve-disorders/multiple-mononeuropathy?query=multiplemononeuropathy>.*
Tsuen-ni, L. U. N. G. "The Culturing of Ericerus pela (Chavannes) in China and the Transmission of Chinese Wax into Europe [J]." Agricultural History of China 4 (2004).*
XianRong Qi and XiaoPing Lei, "Pharmacy and Medicinal Chemistry Sprint Collection", Peking University Medical Press, May 2012, Cover pages and pp. 21-34.

* cited by examiner

*Primary Examiner* — John Pak
*Assistant Examiner* — Daniel L Branson
(74) *Attorney, Agent, or Firm* — JCIPRNET

(57) ABSTRACT

The present invention discloses a rice bran sterol sugar-coated tablet comprising rice bran sterol, a filler and a coating agent, wherein a mass ratio of the rice bran sterol, the filler and the coating agent is 1:3.9-4.5:1.30-1.35. The filler is composed of starch, dextrin, talcum powder, calcium carbonate, microcrystalline cellulose, starch slurry, carboxymethyl starch sodium, magnesium stearate and silicon dioxide in a mass ratio of 1.29-1.5:0.5-0.71:1:1:0.24-0.25:1.86-2.25:0.16-0.18:0.028-0.03:0.14-0.17, and the coating agent is composed of white sugar, gum, gelatin, pigment and Chinese insect wax in a mass ratio of 201-249:5.56-8:1:0.06-0.07:1. The rice bran sterol sugar-coated tablet may be used for treating periodontitis and acute pharyngolaryngitis and has obvious treatment effects on peniculus system inflammations, and is harmless to the human body.

10 Claims, No Drawings

RICE BRAN STEROL SUGAR-COATED TABLET

CROSS-REFERENCE TO RELATED APPLICATION

This is a continuation of International Application No. PCT/CN2017/083509, filed on May 8, 2017, which claims the priority benefits of China Application No. 201611061181.4, filed on Nov. 28, 2016. The entirety of each of the above-mentioned patent applications is hereby incorporated by reference herein and made a part of this specification.

BACKGROUND

1. Field of the Invention

The present invention relates to the technical field of anti-inflammatory drugs, and more particularly, to a rice bran sterol sugar-coated tablet.

2. Description of Related Art

Periodontitis, which is a kind of chronic infectious disease related to periodontal support tissues, is mainly attributable to microorganisms present in the dental plaque, which may subject periodontal support tissues to inflammations and destruction. If gingivitis fails to receive timely treatment, the inflammation may further spread from gingivae to periodontal ligaments, alveolar bones and cementum, thus progressing into periodontitis.

Acute pharyngolaryngitis, which is generally caused by viruses or bacteria, refers to an acute inflammation afflicting pharyngolaryngeal mucosas, submucous tissues and lymphatic tissues. It results, in most cases, from acute rhinitis, acute sinusitis and acute tonsillitis, and is generally complicated by such infectious diseases as measles, influenza and scarlatina. Chronic pharyngolaryngitis refers to a diffuse inflammation afflicting pharyngeal mucosas, submucous tissues and lymphatic tissues. It is a very common pharyngeal disease among people that often occurs with upper respiratory diseases. Moreover, it is also possible that chronic pharyngolaryngitis may be attributable to acute pharyngolaryngitis recurring due to inadequate treatment.

The inflammation caused by periodontitis is generally diminished using antibiotic drugs. Despite relatively good anti-inflammatory effects, antibiotic drugs have adverse effects on human health due to their numerous side effects. Therefore, an anti-inflammatory drug having relatively good eliminating effects on such symptoms as periodontitis and acute pharyngolaryngitis and causing no harm to the human body is commercially valuable to some extent.

SUMMARY

In view of the drawbacks existing in the prior art, it is a first object of the present invention to provide a rice bran sterol sugar-coated tablet, which overcomes the problem that employing antibiotics to eliminate inflammations exerts adverse effects on human health, and is thus of better anti-inflammatory effects and harmless to the human body.

In order to achieve the first object mentioned above, the present invention provides the following technical solution.

A rice bran sterol sugar-coated tablet is provided, which comprises a host material composed of rice bran sterol technical materials, and an auxiliary material comprising a filler and a coating agent, wherein a mass ratio of the host material, the filler and the coating agent is 1:3.9-4.5:1.30-1.35, the filler is composed of starch, dextrin, talcum powder, calcium carbonate, microcrystalline cellulose, starch slurry, carboxymethyl starch sodium, magnesium stearate and silicon dioxide in a mass ratio of 1.29-1.5:0.5-0.71:1:1:0.24-0.25:1.86-2.25:0.16-0.18:0.028-0.03:0.14-0.17, and the coating agent is composed of white sugar, gum, gelatin, pigment and Chinese insect wax in a mass ratio of 201-249:5.56-8:1:0.06-0.07:1; and the structural formula of the rice bran sterol technical materials is as follows:

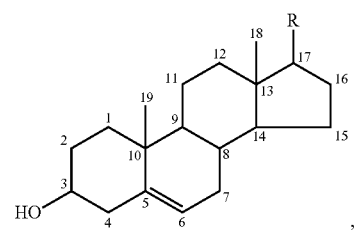

and R is one of

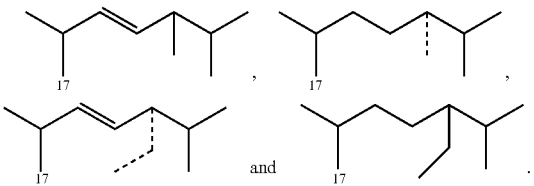

With the above technical solution, rice bran sterol technical materials are extracted from rice bran oil, which are safe and reliable, and cause no harm to the human body. Moreover, calculated on the dried basis, they contain no less than 90% of the total weight of unsaponifiable matters, wherein the amount of sterol is not less than 60%. Besides, rice bran sterol technical materials also contain hydrocarbons, higher fatty acid, triterpene alcohol and vitamins etc., thereby possessing better effects on inflammation resistance, bacterial growth retardation and oxidation resistance. Dextrin is more susceptible to digestion and decomposition by amylase in the intestines and stomach than starch, thereby facilitating absorption by the intestines and stomach. Calcium carbonate may supplement the calcium content of the human body, which, when used in combination with silicon dioxide, may also reduce the viscosity of rice bran sterol raw materials, thus facilitating production. Magnesium stearate may function excellently as lubricant, anti-adherent and glidant, which facilitates thorough mixing of the host material with the auxiliary material. Microcrystalline cellulose may function excellently as diluent and binder, and possesses lubricating and disintegrating effects. When used in combination with magnesium stearate, it may facilitate rapid forming of the rice bran sterol sugar-coated tablet of the present invention in the preparation process. Carboxymethyl starch sodium is odorless, tasteless and non-toxic, which tends to absorb moisture. After being dissolved in water, it forms into a colloidal solution stable to light and heat. Carboxymethyl starch sodium, starch slurry and microcrystalline cellulose may be used in cooperation with one another to increase the viscosity of the formed bulk, and meanwhile, attain good dispersion effects to prevent blockshaped accumulated solids from being formed. Meanwhile, they may also cooperate with one another to form a membranoid substance, thereby playing a role in protecting various components in the present application. However, when entering the intestines and stomach, the formed membranoid substance, under the degradation action of amylase and the like, may be destroyed. As such, the rice bran sterol sugar-coated tablet in the present application is enabled to take effect to play a role in resisting against inflammations. Furthermore, rice bran sterol technical materials, carboxymethyl starch sodium, starch slurry, microcrystalline cellulose and magnesium stearate may also be used in cooperation with one another to treat such symptoms as drying, itching, swelling and aching and the like afflicting the throat due to acute and chronic pharyngolaryngitis as well as common cold, and their treatment effects on pharyngeal membrane system inflammations are remarkable. The sugar coating formed by the coating agent plays a role in coating a tablet, such that the tablet, after being swallowed down by a patient, cannot be prone to take effect immediately during swallowing; more importantly, it also has protective effects on the tablet so as to reduce its risk of being damped. Meanwhile, sugar coatings may improve the mouthfeel of the drug, such that a patient wouldn't find it difficult to swallow it down as its taste has been improved.

The unsaponifiable matters and the sterol which are extracted from the rice bran sterol-series rice bran oil belong to a tetracyclic triterpenoids compound which is widespread in various types of plant oil and plant seeds such as nuts in the natural world, and are convenient to extract. It contains main components of sitosterol, stigmasterol and campesterol; when R is

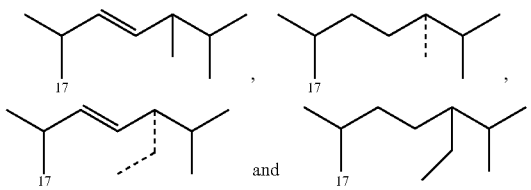

respectively, the rice bran sterol technical materials are brassicasterol, campesterol, stigmasterol and ß-sitosterol respectively. The rice bran sterol technical materials may directly work on a nerve part due to the characteristic of their structural formula, thereby achieving inflammation diminishing and pain alleviating effects on nerves, and fulfilling the aim of treating scapulohumeral periarthritis, cervical pain and all types of neurodynia.

The rice bran sterol sugar-coated tablet may be further used for treating swelling and pain in gums, swelling and pain in throat, kids' cold, allergic cough and the like. In addition, the rice bran sterol sugar-coated tablet may be used for external application after being ground, and drugs may enter the mucosa of the skin due to the characteristic of the rice bran sterol, thereby achieving an effect of treating allergic dermatitis. Therefore, the rice bran sterol sugar-coated tablet may be used for both oral administration and external application to achieve a purpose of treating various diseases.

It is further preferred that the mass ratio of the host material, the filler and the coating agent is 1:4.0-4.3:1.32-1.34.

With the above technical solution, it has been found through research that the host material, the filler and the coating agent, with their respective weights falling within this matching ratio, may be endowed with better anti-inflammatory effects.

It is further preferred that the filler is composed of starch, dextrin, talcum powder, calcium carbonate, microcrystalline cellulose, starch slurry, carboxymethyl starch sodium, magnesium stearate and silicon dioxide in a mass ratio of 1.33-1.45:0.55-0.67:1:1:0.243-0.249:1.90-2.22:0.163-0.178:0.0285-0.0297:0.145-0.166.

With the above technical solution, it has been found through research that starch, dextrin, talcum powder, calcium carbonate, microcrystalline cellulose, starch slurry, carboxymethyl starch sodium, magnesium stearate and silicon dioxide, with their respective weights falling within this matching ratio, may form uniform tablets that cannot break or stick together easily, thereby maintaining a better tablet shape.

It is further preferred that the coating agent is composed of white sugar, gum, gelatin, pigment and Chinese insect wax in a mass ratio of 208-240:5.61-7.8:1:0.062-0.068:1.

With the above technical solution, the formed coating agent is coated on the surface of a tablet. As such, it may have better protective effects on the tablet, and keep the properties thereof stable, such that the tablet cannot take effect until it enters the intestines and stomach, thereby helping protect the esophagus.

It is further preferred that the rice bran sterol sugar-coated tablet is prepared through the following steps:

S1. respectively grinding starch, dextrin, talcum powder, calcium carbonate and microcrystalline cellulose with a 40-mesh grinder, and then thoroughly mixing them to form a first mixture;

S2. grinding rice bran sterol technical materials with the 40-mesh grinder, and then thoroughly mixing them with the first mixture obtained in the S1 to form a second mixture;

S3. placing the second mixture obtained in the S2 into a wet-type granulator, and then adding starch slurry to make them into a soft material;

S4. placing the soft material obtained in the S3 into an oscillating granulator to be made into wet granules, drying the wet granules at 60-90° C., and then screening them with a 10-16 mesh sieve to obtain dried granules;

S5. placing carboxymethyl starch sodium, magnesium stearate and silicon dioxide into a main mixer to be evenly mixed so as to form a third mixture;

S6. achieving thorough mixing of the third mixture obtained in the S5 with the dried granules obtained in the S4 in the main mixer so as to form a fourth mixture;

S7. punching, via an 8-9 mm puncher, the fourth mixture obtained in the S6 into plain tablets, wherein each of the plain tablets has a weight of 170 mg;

S8. placing white sugar, gum, gelatin, pigment and Chinese insect wax into a coating pan, and then thoroughly mixing them to form a coating agent;

S9. placing the plain tablets obtained in the S7 into the coating agent obtained in the S8, and then thoroughly mixing them to obtain a final product.

With the above technical solution, such fillers as starch, dextrin, talcum powder, calcium carbonate and microcrystalline cellulose as well as rice bran sterol technical materials are first ground respectively, and then, they are mixed together. In this manner, various raw materials after grinding can be easily mixed thoroughly. Starch slurry has good viscosity, which, after its mixing with the second mixture that has been thoroughly mixed, may be in bonding connection with the second mixture, such that the formed soft material cannot scatter easily. Carboxymethyl starch sodium, magnesium stearate and silicon dioxide are subjected to adhesion with dried granules so as to reduce surface viscosity thereof, thus separating them from one another, and making it difficult for them to cluster together. As plain tablets are added after white sugar, gum, gelatin, pigment and Chinese insect wax have been thoroughly mixed together, components in various coating agents are allowed to be evenly mixed together, and coated uniformly on the surface of each plain tablet. As such, the formed rice bran sterol sugar-coated tablet has a surface of better glossiness and smoothness, thereby enabling a patient to take it successfully.

It is further preferred that the starch slurry in the S3 has a mass concentration of 5-10%.

With the above technical solution, the formed soft material cannot be prone to be excessively sticky or dried, and is thus prevented from being incompact. As such, it cannot readily adhere to the inner wall of the oscillating granulator in the production process of wet granules, thus reducing wastage of raw materials, and increasing the amount of wet granules produced in the same batch.

It is a second object of the present invention to provide combined administration of rice bran sterol sugar-coated tablet with oryzanol tablet.

In order to achieve the second object mentioned above, the present invention provides the following technical solution:

a drug combined with an oryzanol tablet to treat specific symptoms includes the above-mentioned rice bran sterol sugar-coated tablet.

With the above technical solution, the oryzanol tablet has an anti-oxidization effect, and may adjust nerves and regulate immunity.

Both oryzanol in the oryzanol tablet and rice bran sterol in the rice bran sterol sugar-coated tablet are unsaponifiable matters and sterol extracted from rice bran oil, which have been taken as drugs and used for treatment in China since the 1980s. In addition to having multiple physiological effects such as resistance against oxidation and aging, oryzanol also plays a role in improving vegetative nerve functions and regulating internal secretion. Moreover, oryzanol may function to stabilize emotions, alleviate anxiety and tension, and improve sleep quality, and is thus commonly used to help treat premenstrual and menopausal syndromes. The combined administration of rice bran sterol sugar-coated tablet with oryzanol tablet, which has been clinically used by the inventor and his family members as well as many other people for more than ten years, is found to be able to treat pharyngolaryngitis, allergic dermatitis and testicular inflammations, and improve and alleviate symptoms of a cold.

In conclusion, the present invention has the following beneficial effects:

1. The sterol substances in the present application may act to resist against oxidation and inflammations and retard bacterial growth. It may also be used to relieve such symptoms as drying, itching, swelling and aching and the like afflicting the throat due to acute and chronic pharyngolaryngitis as well as common cold, which has a high level of safety and is harmless to the human body;

2. The rice bran sterol sugar-coated tablet in the present application is coated externally with a sugar coating, which may be effective in moisture resistance, thus making the properties of the tablet more stable; moreover, the sugar coating can improve the appearance and flavor of the tablet, thereby enabling it to be accepted and taken by different groups of people;

3. The addition of calcium carbonate into the rice bran sterol sugar-coated tablet of the present application may, on one hand, supplement the calcium content of the human body and, on the other hand, reduce the viscosities of the host material and the auxiliary material, thereby facilitating production;

4. Carboxymethyl starch sodium, starch slurry and microcrystalline cellulose may be used in cooperation with one another to form a membranoid substance, thereby playing a role in protecting various components in the present application; when entering the intestines and stomach, the formed membranoid substance, under the degradation action of amylase and the like, may be destroyed. As such, the rice bran sterol sugar-coated tablet in the present application is enabled to take effect to play a role in resisting against inflammations;

5. The combined administration of rice bran sterol sugar-coated tablet with oryzanol tablet is found to be able to treat pharyngolaryngitis, allergic dermatitis and testicular inflammations, and improve and alleviate symptoms of a cold;

6. The rice bran sterol sugar-coated tablet has the effects of achieving inflammation diminishing and pain alleviating effects on nerves, thereby fulfilling the aim of treating scapulohumeral periarthritis, cervical pain and all types of neurodynia;

7. The rice bran sterol sugar-coated tablet may be used for external application after being ground, and drugs may enter the mucosa of the skin due to the characteristic of the rice bran sterol, thereby achieving the effect of treating allergic dermatitis.

DESCRIPTION OF THE EMBODIMENTS

The present invention is described below in detail in combination with embodiments.

Embodiment 1

A rice bran sterol sugar-coated tablet was provided, which was prepared through the following steps:

S1. respectively grinding starch, dextrin, talcum powder, calcium carbonate and microcrystalline cellulose with a 40-mesh grinder, and then thoroughly mixing them to form a first mixture;

S2. grinding rice bran sterol technical materials with the 40-mesh grinder, and then thoroughly mixing them with the first mixture obtained in the S1 to form a second mixture;

S3. placing the second mixture obtained in the S2 into a wet-type granulator, and then adding starch slurry with a mass concentration of 8% to make them into a soft material;

S4. placing the soft material obtained in the S3 into an oscillating granulator to be made into wet granules, drying the wet granules at 60-90° C., and then screening them with a 10-16 mesh sieve to obtain dried granules;

S5. placing carboxymethyl starch sodium, magnesium stearate and silicon dioxide into a main mixer to be evenly mixed so as to form a third mixture;

S6. achieving thorough mixing of the third mixture obtained in the S5 with the dried granules obtained in the S4 in the main mixer so as to form a fourth mixture;

S7. punching, via a puncher with 9 mm punch marks, the fourth mixture obtained in the S6 into plain tablets, wherein each of the plain tablets has a weight of 170 mg;

S8. placing white sugar, gum, gelatin, pigment and Chinese insect wax into a coating pan, and then thoroughly mixing them to form a coating agent;

S9. placing the plain tablets obtained in the S7 into the coating agent obtained in the S8, and then thoroughly mixing them to obtain a final product.

Here, the components and corresponding masses thereof are shown in Table 1 (in 10,000 tablets).

The structural formula of the rice bran sterol technical materials is follows:

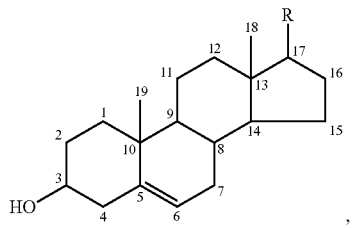

and R is

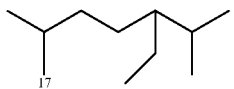

Embodiment 2

A rice bran sterol sugar-coated tablet was provided, which differed from that of Embodiment 1 in that the fourth mixture obtained in the S6 was punched into plain tablets via a puncher with 8.5 mm punch marks, wherein each of the plain tablets had a weight of 170 mg. The components and corresponding masses thereof are shown in Table 1.

Embodiment 3

A rice bran sterol sugar-coated tablet was provided, which differed from that of Embodiment 1 in that the fourth mixture obtained in the S6 was punched into plain tablets via a puncher with 8 mm punch marks, wherein each of the plain tablets had a weight of 170 mg. The components and corresponding masses thereof are shown in Table 1.

Embodiment 4

A rice bran sterol sugar-coated tablet was provided, which differed from that of Embodiment 2 lies in the components and the corresponding masses. The components and corresponding masses thereof are shown in Table 1.

Embodiment 5

A rice bran sterol sugar-coated tablet was provided, which differed from those of Embodiment 2 and Embodiment 1 lies in the components and the corresponding masses. The components and corresponding masses thereof are shown in Table 1.

Embodiment 6

A rice bran sterol sugar-coated tablet was provided, which differed from that of Embodiment 2 in that the rice bran sterol sugar-coated tablet did not contain carboxymethyl starch.

Embodiment 7

A rice bran sterol sugar-coated tablet was provided, which differed from that of Embodiment 2 in that the content of carboxymethyl starch was 25 g (in 10,000 tablets).

Embodiment 8

A rice bran sterol sugar-coated tablet was provided, which differed from that of Embodiment 2 in that the contents of carboxymethyl starch, starch slurry and microcrystalline cellulose were respectively 20 g, 400 g and 25 g (in 10,000 tablets).

Embodiment 9

A rice bran sterol sugar-coated tablet was provided, which differed from that of Embodiment 8 in that the content of rice bran sterol technical materials was 200 g (in 10,000 tablets).

Embodiment 10

A rice bran sterol sugar-coated tablet was provided, which differed from that of Embodiment 8 in that the content of rice bran sterol technical materials was 200 g, and the content of magnesium stearate was 3 g (in 10,000 tablets).

TABLE 1

Various Components in Embodiments 1-5 and Corresponding Masses Thereof

| Components | 1 | 2 | 3 | 4 | 5 |
|---|---|---|---|---|---|
| | Masses (g) | | | | |
| Rice Bran Sterol Technical Material | 350 | 400 | 500 | 450 | 420 |
| Starch | 300 | 390 | 450 | 350 | 410 |
| Dextrin | 100 | 120 | 250 | 200 | 170 |
| Talcum Powder | 200 | 270 | 350 | 240 | 300 |
| Calcium Carbonate | 200 | 300 | 350 | 250 | 300 |
| Microcrystalline Cellulose | 50 | 75 | 85 | 65 | 70 |
| Starch Slurry | 450 | 575 | 650 | 520 | 600 |
| Carboxymethyl Starch Sodium | 35.5 | 47.5 | 55.5 | 50.5 | 40.5 |
| Magnesium Stearate | 5 | 9 | 10 | 7 | 8 |
| Silicon Dioxide | 35 | 39 | 50 | 45 | 43 |
| White Sugar | 450 | 525 | 650 | 550 | 500 |
| Gum | 14.5 | 17.5 | 18 | 15.5 | 16.5 |
| Gelatin | 1.8 | 2.5 | 3.2 | 2.8 | 3 |
| Pigment | 0.1 | 0.2 | 0.2 | 0.1 | 0.15 |
| Chinese Insect Wax | 1.8 | 2.5 | 3.2 | 2.8 | 3 |

Experiment 1

Experiment Samples: Drugs prepared in Embodiments 1-10 were taken as Experiment Samples 1-10.

Experiment Method: 1,000 patients of similar age, who had similar physical conditions and whose throats were afflicted by similar symptoms of drying, itching and swelling and aching induced by periodontitis, acute pharyngolaryngitis and common cold, were selected from the same area, and divided equally into 10 groups marked respectively as 1-10. Groups 1-10 were treated using Experiment Samples 1-10 respectively, and the patient's recovery conditions were observed and recorded for a week.

Experiment Results: The recovery conditions of the patients taking Experiment Samples 1-10 for a week are as shown in Table 2.

TABLE 2

Recovery Conditions of the Patients Taking Experiment Samples 1-10 for a Week

| Experiment Sample | Symptom | | | | |
|---|---|---|---|---|---|
| | Periodontitis | Acute Pharyngolaryngitis | Throat Drying | Throat Itching | Throat Swelling and Aching |
| | Recovery Number of People (Person) | | | | |
| 1 | 100 | 99 | 96 | 97 | 99 |
| 2 | 100 | 100 | 99 | 98 | 100 |
| 3 | 100 | 100 | 98 | 98 | 99 |
| 4 | 100 | 100 | 97 | 97 | 100 |
| 5 | 100 | 99 | 96 | 99 | 99 |
| 6 | 63 | 59 | 61 | 57 | 58 |
| 7 | 68 | 62 | 65 | 62 | 63 |
| 8 | 72 | 66 | 71 | 68 | 73 |
| 9 | 55 | 32 | 17 | 24 | 28 |
| 10 | 50 | 49 | 41 | 43 | 42 |

As can be known from Table 2, for patients treated with Experiment Samples 1-5, the healing rate of drying, itching and swelling and aching afflicting their throats due to periodontitis, acute pharyngolaryngitis and common cold is high, and they are almost completely healed. During taking, the drugs can be swallowed down easily, and are not prone to get stuck in the esophagus. Moreover, no dizziness, vomiting, stomachache and the like are reported from the patients during treatment. However, for patients treated with Experiment Samples 6-10, the recovery conditions of drying, itching and swelling and aching afflicting their throats due to periodontitis, acute pharyngolaryngitis and common cold are poor, and what's worse is that different levels of dizziness and vomiting are reported from the patients. This indicates that rice bran sterol technical materials, carboxymethyl starch sodium, starch slurry and microcrystalline cellulose may interact with one another to improve the healing rate of periodontitis and treat such symptoms as drying, itching, swelling and aching and the like afflicting the throat due to acute pharyngolaryngitis and common cold, and their treatment effects on pharyngeal membrane system inflammations are also remarkable.

Experiment 2

Experiment Samples: Drugs prepared in Embodiments 1-10 were taken as Experiment Samples 1-10.

Experiment Method: 500 adult patients and 500 child patients (ages ranging from 4 to 12), who were of similar age and had similar physical conditions and identical cold symptoms, were selected from the same area. They were divided equally into 10 groups marked respectively as 1-10, and each group was composed of 50 adult patients and 50 child patients. Groups 1-10 were treated using Experiment Samples 1-10 respectively, wherein the patients in Group 1 only took Experiment Sample 1 orally; the patients in Groups 2-5 orally took oryzanol tablets in addition to Experiment Samples 2-5; the patients in Groups 6-10 only took Samples 6-10 orally.

Here, the dosage of Experiment Sample 1 orally taken by each adult patient in Group 1 was 340 mg on a four-times-a-day basis, while that of Experiment Sample 1 orally taken by each child patient was 200 mg on a three-times-a-day basis.

The dosages of Experiment Sample 2 and oryzanol tablets orally taken by each adult patient in Group 2 were respectively 320 mg and 40 mg on a four-times-a-day basis, while those of Experiment Sample 2 and oryzanol tablets orally taken by each child patient were respectively 200 mg and 20 mg on a three-times-a-day basis.

The dosages of Experiment Sample 3 and oryzanol tablets orally taken by each adult patient in Group 3 were respectively 400 mg and 50 mg on a four-times-a-day basis, while those of Experiment Sample 3 and oryzanol tablets orally taken by each child patient were respectively 200 mg and 20 mg on a three-times-a-day basis.

The dosages of Experiment Sample 4 and oryzanol tablets orally taken by each adult patient in Group 4 were respectively 340 mg and 43 mg on a four-times-a-day basis, while those of Experiment Sample 4 and oryzanol tablets orally taken by each child patient were respectively 200 mg and 20 mg on a three-times-a-day basis.

The dosages of Experiment Sample 5 and oryzanol tablets orally taken by each adult patient in Group 5 were respectively 380 mg and 46 mg on a four-times-a-day basis, while those of Experiment Sample 5 and oryzanol tablets orally taken by each child patient were respectively 200 mg and 20 mg on a three-times-a-day basis.

The dosage of Experiment Sample 6 orally taken by each adult patient in Group 6 was 340 mg on a four-times-a-day basis, while that of Experiment Sample 6 orally taken by each child patient was 200 mg on a three-times-a-day basis.

The dosage of Experiment Sample 7 orally taken by each adult patient in Group 7 was 380 mg on a four-times-a-day basis, while that of Experiment Sample 7 orally taken by each child patient was 200 mg on a three-times-a-day basis.

The dosage of Experiment Sample 8 orally taken by each adult patient in Group 8 was 320 mg on a four-times-a-day basis, while that of Experiment Sample 8 orally taken by each child patient was 200 mg on a three-times-a-day basis.

The dosage of Experiment Sample 9 orally taken by each adult patient in Group 9 was 400 mg on a four-times-a-day basis, while that of Experiment Sample 9 orally taken by each child patient was 200 mg on a three-times-a-day basis.

The dosage of Experiment Sample 10 orally taken by each adult patient in Group 10 was 360 mg on a four-times-a-day basis, while that of Experiment Sample 10 orally taken by each child patient was 200 mg on a three-times-a-day basis.

Rehabilitation conditions of the patients were observed and recorded.

Experiment Results: For Group 1, 92% of the adult patients and 80% of the child patients fully recovered from their cold in the fifth day; for Group 2, 94% of the adult patients and 90% of the child patients fully recovered from their cold in the fourth day; for Group 3, 100% of the adult patients and 88% of the child patients fully recovered from their cold in the fourth day; for Group 4, 96% of the adult patients and 88% of the child patients fully recovered from their cold in the fourth day; for Group 5, 96% of the adult patients and 88% of the child patients fully recovered from their cold in the fourth day; for Group 6, 90% of the adult patients and 86% of the child patients fully recovered from their cold in the eighth day; for Group 7, 94% of the adult patients and 88% of the child patients fully recovered from their cold in the eighth day; for Group 8, 92% of the adult patients and 88% of the child patients fully recovered from their cold in the eighth day; for Group 9, 90% of the adult patients and 86% of the child patients fully recovered from their cold in the ninth day; for Group 10, 92% of the adult patients and 88% of the child patients fully recovered from their cold in the eighth day. No side effects were reported from the child patients during treatment.

Experiment 3

Experiment Samples: drugs prepared in Embodiments 1-10 were taken as Experiment Samples 1-10.

Experiment Method: 1,000 patients of similar age, who had similar physical conditions and similar symptoms induced by scapulohumeral periarthritis, cervical pain and all types of neuralgia (including trigeminal neuralgia, sciatica, intercostal neuralgia and the like), were selected from the same area, and divided equally into 10 groups marked respectively as 1-10. Groups 1-10 were treated using Experiment Samples 1-10 respectively, and the patient's recovery conditions were observed and recorded for three weeks.

Experiment Results: the recovery conditions of the patients taking Experiment Samples 1-10 for three weeks are as shown in Table 3.

TABLE 3

Recovery Conditions of the Patients Taking Experiment Samples 1-10 for Three Weeks

| Experiment Sample | Symptom | | |
|---|---|---|---|
| | Scapulohumeral Periarthritis | Cervical Pain | All Types of Neuralgia |
| | Recovery Number of People (Person) | | |
| 1 | 99 | 100 | 98 |
| 2 | 100 | 99 | 99 |
| 3 | 99 | 99 | 97 |
| 4 | 100 | 99 | 98 |
| 5 | 99 | 100 | 99 |
| 6 | 66 | 62 | 63 |
| 7 | 69 | 63 | 65 |
| 8 | 75 | 70 | 72 |
| 9 | 62 | 58 | 50 |
| 10 | 65 | 53 | 52 |

As can be known from Table 3, Experiment Samples 1-5 have relatively good curing effects on scapulohumeral periarthritis, cervical pain and all types of neuralgia, wherein there are 99-100 people recovering from scapulohumeral periarthritis and cervical pain, and there are 97-99 people recovering from all types of neuralgia, but Experiment Samples 6-10 have poor curing effects on scapulohumeral periarthritis, cervical pain and all types of neuralgia, and these curing effects are greatly different from those of Experiment Samples 1-5 as there are 62-75 people recovering from scapulohumeral periarthritis, there are 62-70 people recovering from cervical pain, and there are 50-72 people recovering from all types of neuralgia.

Experiment 4

Experiment Samples: drugs prepared in Embodiments 1-10 were taken as Experiment Samples 1-10.

Experiment Method: 1,000 patients of similar age, who had similar physical conditions and similar symptoms induced by allergic dermatitis, were selected from the same area, and divided equally into 10 groups marked respectively as 1-10. Groups 1-10 were treated in a skin surface coating way using Experiment Samples 1-10 respectively according to an affected part coating amount calculated based on 0.2 ml/cm², and the patient's recovery conditions were observed and recorded for a week.

Experiment Results: the recovery conditions of the patients taking Experiment Samples 1-10 for a week are as shown in Table 4.

TABLE 4

Recovery Conditions of the Patients Taking Experiment Samples 1-10 for a Week

| Experiment Sample | symptom<br>Allergic Dermatitis<br>Recovery Number of People (Person) |
|---|---|
| 1 | 100 |
| 2 | 100 |
| 3 | 100 |
| 4 | 100 |
| 5 | 100 |
| 6 | 65 |
| 7 | 68 |
| 8 | 71 |
| 9 | 53 |
| 10 | 50 |

As can be known from Table 4, for patients treated with Experiment Samples 1-5, the recovery rate of allergic dermatitis is the highest, all members in the groups are cured, and no side effects are caused during treatment, but for patients treated with Experiment Samples 6-10, only 50-71% of patients recover from allergic dermatitis.

What have been described above are merely preferred embodiments of the present invention, but the scope of protection of the present invention should not be so limited. All technical solutions that fall within the spirit of the present invention shall be covered by the scope of protection of the present invention. It should be noted that for those of ordinary skill in the art, various improvements and modifications that are made without departing from the principles of the present invention shall also be regarded as being covered by the scope of protection of the present invention.

What is claimed is:
1. A rice bran sterol sugar-coated tablet, comprising:
   a host material comprising rice bran sterol having a chemical formula below

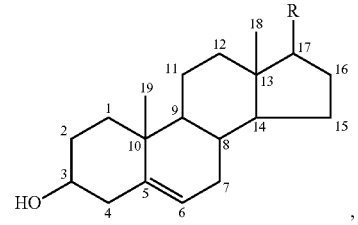

wherein R is one of

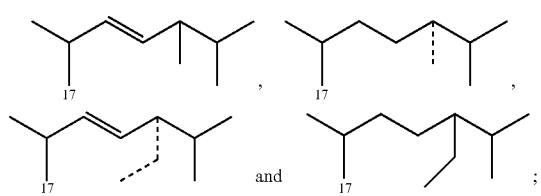

and
an auxiliary material comprising:
a filler comprising starch, dextrin, talcum powder, calcium carbonate, microcrystalline cellulose, starch slurry with a mass concentration of 5-10%, carboxymethyl starch sodium, magnesium stearate and silicon dioxide mixed in a mass ratio of 1.29-1.5:0.5-0.71:1:1:0.24-0.25:1.86-2.25:0.16-0.18:0.028-0.03:0.14-0.17; and a coating agent comprising white sugar, gum, gelatin, pigment and cera chinensis mixed in a mass ratio of 201-249:5.56-8:1:0.06-0.07:1, and wherein a mass ratio of the host material, the filler and the coating agent is 1:3.9-4.5:1.30-1.35.

2. The rice bran sterol sugar-coated tablet of claim 1, wherein the mass ratio of the host material, the filler and the coating agent is 1:4.0-4.3:1.32-1.34.

3. The rice bran sterol sugar-coated tablet of claim 1, wherein the filler comprises the starch, the dextrin, the talcum powder, the calcium carbonate, the microcrystalline cellulose, the starch slurry, the carboxymethyl starch sodium, the magnesium stearate and the silicon dioxide mixed in a mass ratio of 1.33-1.45:0.55-0.67:1:1:0.243-0.249:1.90-2.22:0.163-0.178:0.0285-0.0297:0.145-0.166.

4. The rice bran sterol sugar-coated tablet of claim 1, wherein the coating agent comprises the white sugar, the gum, the gelatin, the pigment and the cera chinensis mixed in a mass ratio of 208-240:5.61-7.8:1:0.062-0.068:1.

5. The rice bran sterol sugar-coated tablet of claim 1, wherein the rice bran sterol sugar-coated tablet is prepared by the following steps:
(S1) respectively grinding the starch, the dextrin, the talcum powder, the calcium carbonate and the microcrystalline cellulose, and then thoroughly mixing the starch, the dextrin, the talcum powder, the calcium carbonate and the microcrystalline cellulose to form a first mixture;
(S2) grinding the host material, and then thoroughly mixing the host material with the first mixture to form a second mixture;
(S3) adding starch slurry to the second mixture, and then mixing the starch slurry and the second mixture to form a soft material;
(S4) making wet granules by the soft material, and then drying the wet granules at 60-90° C. to obtain dried granules;
(S5) evenly mixing carboxymethyl starch sodium, magnesium stearate and silicon dioxide to form a third mixture;
(S6) mixing the third mixture and the dried granules to form a fourth mixture;
(S7) punching the fourth mixture into plain tablets;
(S8) thoroughly mixing the white sugar, the gum, the gelatin, the pigment and the cera chinensis to form a coating agent, wherein the white sugar, the gum, the gelatin, the pigment and the cera chinensis mixed in the mass ratio of 201-249:5.56-8:1:0.06-0.07:1; and
(S9) placing the plain tablets into the coating agent, and then thoroughly mixing the plain tablets and the coating agent to obtain a final product,
wherein the starch, the dextrin, the talcum powder, the calcium carbonate, the microcrystalline cellulose, the starch slurry, the carboxymethyl starch sodium, the magnesium stearate and the silicon dioxide mixed in the mass ratio of 1.29-1.5:0.5-0.71:1:1:0.24-0.25:1.86-2.25:0.16-0.18:0.028-0.03:0.14-0.17,
wherein the mass ratio of the host material, the filler and the coating agent is 1:3.9-4.5:1.30-1.35.

6. A pharmaceutical composition comprising the rice bran sterol sugar-coated tablet of claim 1 combined with an oryzanol tablet for treating symptoms of periodontitis, acute pharyngolaryngitis, common cold induced throat drying, throat itching, throat swelling and throat aching, scapulohumeral periarthritis, cervical pain, neuralgia comprising trigeminal neuralgia, sciatica, and intercostal neuralgia, and allergic dermatitis.

7. A pharmaceutical composition comprising the rice bran sterol sugar-coated tablet of claim 2 combined with an oryzanol tablet for treating symptoms of periodontitis, acute pharyngolaryngitis, common cold induced throat drying, throat itching, throat swelling and throat aching, scapulohumeral periarthritis, cervical pain, neuralgia comprising trigeminal neuralgia, sciatica, and intercostal neuralgia, and allergic dermatitis.

8. A pharmaceutical composition comprising the rice bran sterol sugar-coated tablet of claim 3 combined with an oryzanol tablet for treating symptoms of periodontitis, acute pharyngolaryngitis, common cold induced throat drying, throat itching, throat swelling and throat aching, scapulohumeral periarthritis, cervical pain, neuralgia comprising trigeminal neuralgia, sciatica, and intercostal neuralgia, and allergic dermatitis.

9. A pharmaceutical composition comprising the rice bran sterol sugar-coated tablet of claim 4 combined with an oryzanol tablet for treating symptoms of periodontitis, acute pharyngolaryngitis, common cold induced throat drying, throat itching, throat swelling and throat aching, scapulohumeral periarthritis, cervical pain, neuralgia comprising trigeminal neuralgia, sciatica, and intercostal neuralgia, and allergic dermatitis.

10. A pharmaceutical composition comprising the rice bran sterol sugar-coated tablet of claim 5 combined with an oryzanol tablet for treating symptoms of periodontitis, acute pharyngolaryngitis, common cold induced throat drying, throat itching, throat swelling and throat aching, scapulohumeral periarthritis, cervical pain, neuralgia comprising trigeminal neuralgia, sciatica, and intercostal neuralgia, and allergic dermatitis.

* * * * *